United States Patent [19]

Hoffman et al.

[11] Patent Number: 5,239,088
[45] Date of Patent: Aug. 24, 1993

[54] PROCESS FOR THE PREPARATION OF HOMOSERINE LACTONES

[75] Inventors: Michael G. Hoffman, Hofheim am Taunus; Hans-Joachim Zeiss, Sulzbach/Taunus, both of Fed. Rep. of Germany

[73] Assignee: Hoechst Aktiengesellschaft, Frankfurt am Main, Fed. Rep. of Germany

[21] Appl. No.: 832,120

[22] Filed: Feb. 6, 1992

[30] Foreign Application Priority Data

Feb. 8, 1991 [DE] Fed. Rep. of Germany ....... 4103821

[51] Int. Cl.$^5$ .......................................... C07D 305/12
[52] U.S. Cl. ................................................... 549/321
[58] Field of Search ....................................... 549/321

[56] References Cited

FOREIGN PATENT DOCUMENTS 48-18229 3/1973 Japan .
48-76857 10/1973 Japan .
59-148773 8/1984 Japan .................................. 549/321

OTHER PUBLICATIONS

H, Sugano et al., Bull. Chem. Soc. Japan, vol. 46, (1973), p. 669 ff.
J. E. Baldwin et al., Tetrahedron, vol. 44, No. 2, (1988), p. 637 ff.
B. Gong et al., J. Org. Chem., vol. 55, (1990), p. 4763 ff.
B. H. Lee et al., "Constituents of Microbial Iron Chelators. The Synthesis of Optically Active Derivatives on δ-N-Hydroxy-L-Ornithine", Tetrahedron Letters, vol. 25, No. 9, pp. 927-930, (1984).
J. E. Baldwin et al., "Synthesis of Bicyclic γ-Lactams Via Oxazolidinones", Tetrahedron, vol. 42, No. 23, pp. 6551 to 6554, (1986).
G. Bold et al., "43. Herstellung von Semialdehyd-'-Derivaten von Asparaginsäure-und Glutaminsäure durch Rosenmund-Reduktion", Helvetica Chimica Acta, vol. 73, pp. 405 to 410, (1990).
Babad et al., Synthesis, 966-968 (1988).
Nagase et al., Chemistry Letters, 1695-1698 (1988).
Tsuji et al., Chemistry Letters, 1085-1086 (1977).
Scholtz et al., Synthesis, 542-544 (1989).
Micheel et al., Chem. Ber. 95, 1009-1015 (1962).
Coffey, Chemical Communications, 923 (1967).

Primary Examiner—C. Warren Ivy
Assistant Examiner—Raymond Covington
Attorney, Agent, or Firm—Curtis, Morris & Safford

[57] ABSTRACT

α-Amino-γ-butyrolactones (homoserine lactones) are a central structural element in many biologically active compounds. The known syntheses for the preparation of optically active homoserine lactones from D- or L-methionine and D- or L-aspartic acid derivatives have disadvantages. Homoserine lactones I and their salts can be prepared enantioselectively according to the invention by catalytic hydrogenation of aldehydes II

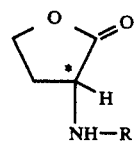

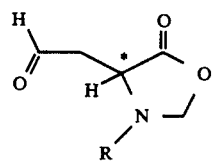

where R in the formulae is hydrogen, alkyl, alkenyl, alkynyl, it being possible for the aforementioned three radicals to have hetero atoms in the chain, alkylcarbonyl, alkoxycarbonyl, alkylsulfonyl, benzyl, benzyloxycarbonyl, aryloxycarbonyl or arylsulfonyl, it being possible for the four last-mentioned radicals to be optionally substituted in the aryl moiety.

21 Claims, No Drawings

PROCESS FOR THE PREPARATION OF HOMOSERINE LACTONES

The present invention relates to a process for the enantioselective synthesis of homoserine lactones of the formula I

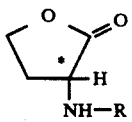
(I)

in which

R is hydrogen, alkyl, alkenyl, alkynyl, it being possible for the aforementioned three radicals to have hetero atoms in the chain, alkylcarbonyl, alkoxycarbonyl, alkylsulfonyl, benzyl, benzyloxycarbonyl, aryloxycarbonyl or arylsulfonyl, it being possible for the four last-mentioned radicals to be optionally substituted in the aryl moiety,
and the salts thereof with inorganic or organic acids or bases.

α-Amino-γ-butyrolactones (homoserine lactones) are a central structural element in many biologically active compounds. Thus, for example, they occur as important structural components in renin inhibitors (WO 8705909), ACE inhibitors (EP-A-266568) and in fungicides (EP-A-51742 or DE-A-2804299). They can also be employed as sedatives (EP-A-151964) and for the treatment of alcoholism (EP-A-144812). In addition, optically active homoserine lactones are valuable synthons for the preparation of enantiomerically pure derivatives. Thus, for example, they can also be converted into the corresponding homoserine derivatives which, in their turn, are then also important structural elements of biologically active compounds (Tetrahedron Lett. 1978 (26) 2243-2246).

The syntheses hitherto disclosed for the preparation of optically active homoserine lactones are associated with disadvantages.

Thus, the processes which start from optically active methionine derivatives have the disadvantage that D- and L-methionine are relatively costly or difficult to obtain. Additional factors are the high price and the extremely high toxicity of iodomethane which is employed in these processes (JP-48076857 (Derwent V 4816 (1974)), JP-48018229 (Derwent V 14063 (1974)), Bull. Chem. Soc. 46, 669 (1973)).

Furthermore, there are descriptions in the literature of processes which, starting from D- or L-aspartic acid derivatives, lead, via a reduction with metal hydrides, to optically active homoserine lactones (Tetrahedron 1988, 637; J. Org. Chem. 1990, 55, 4763). These processes are not worthwhile from the economic viewpoint because of the high costs of the complex metal hydrides to be employed and the difficulties with disposing of their wastes.

A process which makes it possible to synthesize homoserine lactones from low-cost and easily obtainable starting materials is therefore in demand and is of considerable advantage.

The present invention relates to a process for the preparation of racemic or optically active homoserine lactones of the said formula I, which comprises racemic or optically active aldehydes of the formula II

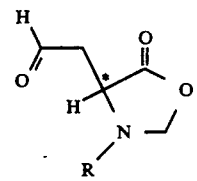
II in which R has the same meaning as in formula I, being hydrogenated in the presence of a catalyst suitable for the hydrogenation.

The process according to the invention represents a catalytic hydrogenation of the aldehyde group to the alcohol and, with opening of the oxazolidine ring and elimination of formaldehyde, a lactonization.

Alkyl, alkenyl and alkynyl in the formulae are straight-chain or branched. A corresponding statement applies to the alkyl radicals in the composite groups such as alkylcarbonyl, alkoxycarbonyl, alkylsulfonyl etc.; examples of meanings of alkyl are methyl, ethyl, n- and i-propyl, n-, i-, t- and 2-butyl, pentyls, hexyls such as n-hexyl, i-hexyl and 1,3-dimethylbutyl, heptyls such as n-heptyl, 1-methylhexyl and 1,4-dimethylpentyl; examples of meanings of alkenyls are allyl, 1-methyl-2-propenyl, 2-butenyl, 3-butenyl, 1-methyl-3-butenyl and 1-methyl-2-butenyl; examples of meanings of alkynyl are propargyl, 2-butynyl, 3-butynyl, 1-methyl-3-butynyl; examples of meanings of aryl are phenyl, naphthyl, thienyl and other heteroaryls; optionally substituted aryl is, for example, aryl which is unsubstituted or substituted one or more times by radicals from the group comprising halogen, alkyl, alkoxy, halogenoalkyl, halogenoalkoxy and nitro.

R in the formula I is preferably hydrogen, $C_1-C_6$-alkyl, $C_2-C_6$-alkenyl, $C_2-C_5$-alkynyl, it being possible for the three last-mentioned radicals to contain hetero atoms, for example in the form of one or more divalent groups such as —O—, —S—, —N— and —N(CH$_3$)—, in the chain, or ($C_1-C_6$-alkyl)-carbonyl, ($C_1-C_6$-alkoxy)-carbonyl, benzyl, benzyloxycarbonyl, phenyloxycarbonyl or phenylsulfonyl, where the four last-mentioned radicals are unsubstituted or substituted by one or more radicals from the group comprising halogen, $C_1-C_4$-alkyl, $C_1-C_4$-alkoxy, $C_1-C_4$-halogenoalkyl, $C_1-C_4$-halogenoalkoxy and nitro in the phenyl moiety.

R is, in particular, hydrogen, $C_1-C_4$-alkyl, $C_2-C_4$-alkenyl, $C_2-C_4$-alkynyl, ($C_1$-C-alkyl)-carbonyl, ($C_1-C_4$-alkoxy)carbonyl, benzyl, benzyloxycarbonyl, phenyloxycarbonyl, phenylsulfonyl, where the four last-mentioned radicals are unsubstituted or substituted by one or more radicals from the group comprising methyl, ethyl, methoxy, ethoxy and nitro.

The starting materials of the formula II can be easily obtained by methods known from the literature, for example by a Rosenmund reaction from the corresponding racemic or optically active carbonyl chlorides of the formula III

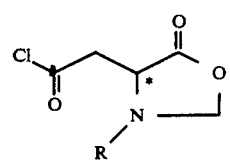
III in which R has the same meaning as in formula I (Helvetica Chim. Acta 73, 405 (1990); Tetrahedron 42 (1986) 6551).

The acid chlorides of the formula III have in some cases been described or can be prepared by methods known from the literature from the corresponding carboxylic acids of the formula IV

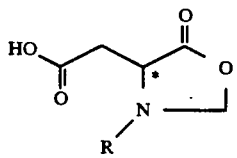

in which R has the same meaning as in formula I (Organikum, VEB Deutscher Verlag der Wissenschaften, Berlin 1976, p. 526; Helvetica Chim. Acta 73 (1990) 405).

The carboxylic acids of the formula IV are in some cases known from the literature or can be prepared by processes known per se from (S)- or (R)-aspartic acid derivatives or mixtures thereof, of the formula V

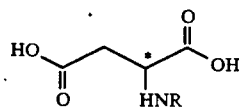

in which R has the same meaning as in formula I (Synthesis 1989, 542; Chem. Ber. 95, 1009 (1962); Tetrahedron 42 (1986) 6551).

Hydrogenations of aldehydes which differ structurally from those of the formula II, in the presence of catalysts, are known (Chem. Commun. 1967, 923; Chemistry Lett. 1988, 1695; Chemistry Lett. 1977, 1085; Synthesis 1988, 966).

However, the process according to the invention is surprising in that, for example, the reduction of the aldehydes of the formula II which contain an α-amino acid group can also be carried out chemoselectively in the presence of a wide variety of radicals R. It is also surprising, furthermore, that the alcohol rearranges, with opening of the oxazolidine ring, to the homoserine lactones of the formula I, and that no racemization takes place in this reaction.

The process according to the invention thus makes it possible, in particular, to prepare optically active homoserine lactones from easily obtainable optically active aspartic acid derivatives in an enantioselective manner. It is preferable to employ optically active starting materials and to obtain optically active compounds of the formula (I), which contain an optical purity of more than 50%, preferably more than 80%, in particular more than 30% (S) form or (R) form.

The process according to the invention can be carried out, for example, in such a way that the aldehydes of the formula II are mixed in a suitable inorganic or organic solvent with a suitable catalyst, and the hydrogenation is carried out at temperatures from 30° to 200° C., preferably at 50° to 150° C., and under a pressure of 1 bar—100 bar, preferably 1 bar—20 bar, of hydrogen.

Suitable solvents are organic solvents form the group of alcohols such as, for example, methanol, ethanol, n- and i-propanol, n- and i-butanol, from the group of aliphatic and aromatic hydrocarbons such as, for example, cyclohexane and petroleum ether or benzene, toluene and xylenes, from the group of ethers such as, for example, (poly)glycol monoalkyl ethers or dialkyl ethers, diethyl ether, tetrahydrofuran and dioxane, and from the group of esters, for example ethyl acetate. Organic solvents such as benzene, toluene and tetrahydrofuran are preferred. It is also possible to employ mixtures of organic solvents.

Suitable catalysts are hydrogenation catalysts which are able under the reaction conditions to catalyze the reduction of an aldehyde functionality to a hydroxymethyl group by hydrogen.

Examples of suitable catalysts are those from the group comprising palladium, ruthenium, iridium and platinum and their complexes or complex salts with inorganic and organic ligands. Particularly suitable are the divalent salts of ruthenium and the trivalent salts of iridium, and the triphenylphosphine complexes thereof are preferably employed. Examples of these are, for example $RuCl_2(PPh_3)$ and $IrH_3(PPh_3)_3$.

The ratio by weight of substrate to catalyst can vary within a wide range and depends, for example, on the individual catalyst and the conversion rate. A ratio which is optimal with regard to required conversion rate and amount of catalyst used can easily be determined in preliminary tests. As a rule, good conversion rates are possible with a catalyst:substrate ratio of from 1:10,000 to 1:20 by weight. In the case of a catalyst complex such as $RuCl_2(PPh_3)_3$, for example, a catalyst:substrate ratio of 1:500 to 1:50 by weight is preferred.

The product can be isolated by customary methods. As a rule, the solvent is removed by distillation under reduced pressure. The crude product, which is, as a rule, solid or an oil, is then, for example, (re)crystallized or chromatographed.

EXAMPLE 1

N-(Benzyloxycarbonyl)-(S)-homoserine lactone

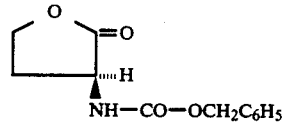

180 ml of benzene, 15.5 g (58.9 mmol) of benzyl (S)-4-(formylmethyl)-5-oxo-1,3-oxazolidine-3-carboxylate and 0.27 g of $RuCl_2(PPh_3)_3$ are introduced successively into a 500 ml steel autoclave (stainless steel), a hydrogen pressure of 10 bar is injected, and the mixture is stirred at 80° C. for 20 h. It is then filtered, and the filtrate is concentrated under water pump vacuum. The crude product obtained in this way is recrystallized from heptane/ethyl acetate; 6.8 g (51% of theory) of the initially identified product are obtained as colorless crystals, melting point: 124°–126° C. $[\alpha]_D^{25} = -30.8°$ (c=1, MeOH); literature data (Bull. Chem. Soc. 46, 669 (1973)): melting point: 126° C.; $[\alpha\ _D^{25} = -30.5°$ (c=1, MeOH).

EXAMPLE 2

N-(p-toluenesulfonyl)-(S)-homoserine lactone

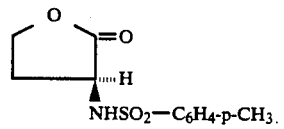

100 ml of benzene, 9.6 g (33.9 mmol) of (S)-4-(formyl-methyl)-3-(p-toluenesulfonyl)-5-oxo-1,3-oxazolidine and 0.17 g of RuCl$_2$(PPh$_3$)$_3$ are introduced successively into a 250 ml steel autoclave (stainless steel), a hydrogen pressure of 10 bar is injected, and the mixture is stirred at 80° C. for 20 h. It is then filtered, and the filtrate is concentrated under water pump vacuum. The crude product obtained in this way is recrystallized from heptane/ethyl acetate; 6 g (70% of theory) of N-(p-toluenesulfonyl)-(S)-homoserine lactone are obtained as colorless crystals. Melting point: 131°–133° C.; $[\alpha]_D^{25} = +8.5°$ (c=1, MeOH); comparison data from the literature (Bull. Chem. Soc. 46, 669 (1973)); melting point: 130°–133° C., $[\alpha]_D^{25} = +8.0°$ (c=1, MeOH).

EXAMPLE 3

N-Methoxycarbonyl-(S)-homoserine lactone

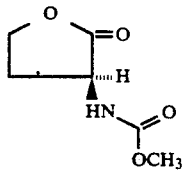

440 ml of benzene, 28 g (150 mmol) of methyl (S)-4-(formylmethyl)-5-oxo-1,3-oxazolidine-3-carboxylate and 0.7 g of RuCl$_2$(PPh$_3$)$_3$ are introduced successively into a 1 l steel autoclave (stainless steel), a hydrogen pressure of 10 bar is injected, and the mixture is stirred at 80° C. for 20 h. It is then filtered, and the filtrate is concentrated under water pump vacuum. The crude product is purified by column chromatography on silica gel (mobile phase: heptane/ethyl acetate=3/7); 17.9 g (75% of theory) of product are obtained as colorless crystals. Melting point: 83°–85° C.; $[\alpha]_D^{25} = -6.5°$ (c=1, CH$_2$Cl$_2$); literature data (Tetrahedron Lett. 30 (1990) 2037); $[\alpha]_D^{25} = -6.8°$ (c=1, CH$_2$Cl$_2$).

We claim:

1. A process for the preparation of racemic or optically active homoserine lactones of the formula I

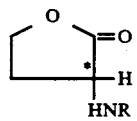

in which

R is hydrogen, alkyl, alkenyl, alkynyl, it being possible for the aforementioned three radicals to have hetero atoms in the chain, alkylcarbonyl, alkoxycarbonyl, alkylsulfonyl, benzyl, benzyloxycarbonyl, aryloxycarbonyl or arylsulfonyl, where the four last-mentioned radicals are unsubstituted or substituted in the aryl moiety, and the salts thereof with inorganic or organic acids or bases, which comprises racemic or optically active aldehydes of the formula II

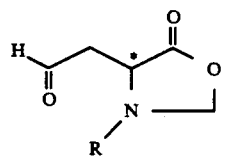

in which R has the same meaning as in formula I, being hydrogenated in the presence of a catalyst suitable for the hydrogenation.

2. The process as claimed in claim 1, wherein R is hydrogen, C$_1$–C$_5$-alkyl, C$_2$–C$_5$-alkenyl, C$_2$–C$_5$-alkynyl, it being possible for the three last-mentioned radicals to contain hetero atoms in the chain, or (C$_1$–C$_6$-alkyl)-carbonyl, (C$_1$–C$_6$-alkoxy)-carbonyl, benzyl, benzyloxycarbonyl, phenyloxycarbonyl or phenylsulfonyl, where the four last-mentioned radicals are unsubstituted or substituted by one or more radicals from the group comprising halogen, C$_1$–C$_4$-alkyl, C$_1$–C$_4$-alkoxy, C$_1$–C$_4$-halogenoalkyl, C$_1$–C$_4$-halogenoalkoxy and nitro in the phenyl moiety.

3. The process as claimed in claim 1, wherein R is hydrogen, C$_1$–C$_4$-alkyl, C$_2$–C$_4$-alkenyl, C$_2$–C$_4$-C -alkynyl, (C$_1$–C$_4$-alkyl)-carbonyl, (C$_1$–C$_4$-alkoxy)-carbonyl, benzyl, benzyloxycarbonyl, phenyloxycarbonyl, phenylsulfonyl, where the four last-mentioned radicals are unsubstituted or substituted by one or more radicals from the group comprising methyl, ethyl, methoxy, ethoxy and nitro.

4. The process as claimed in claim 1, wherein the compounds of the formula I are (S)-homoserine lactones or (R)-homoserine lactones with an optical purity of more than 50% (S) or (R) form.

5. The process as claimed in claim 1, wherein the hydrogenation is carried out in the presence of an organic solvent.

6. The process as claimed in claim 5, wherein the solvent is selected from the group comprising alcohols, aliphatic and aromatic hydrocarbons, ethers and esters and mixtures thereof.

7. The process as claimed in claim 6, wherein the solvent is benzene, toluene, xylene or tetrahydrofuran.

8. The process as claimed in claim 1, wherein the hydrogenation is carried out at 30° to 200° C.

9. The process as claimed in claim 1, wherein the temperature is 50° to 150° C.

10. The process as claimed in claim 1, wherein the hydrogen pressure is 1 to 100 bar.

11. The process as claimed in claim 1, wherein the hydrogen pressure is 1 to 20 bar.

12. The process as claimed in claim 1,
wherein the catalyst is from the group comprising palladium, ruthenium, iridium and platinum and their complexes and complex salts with inorganic or organic ligands.

13. The process as claimed in claim 1, wherein the catalyst is a divalent salt of ruthenium or a trivalent salt of iridium.

14. The process as claimed in claim 1, wherein the catalyst is RuCl$_2$(PPh$_3$)$_3$.

15. The process as claimed in claim 1,
wherein the compounds of the said formula II are prepared from aspartic acid derivatives of the formula V

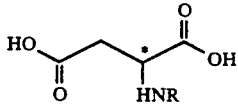 V in which R is defined as in formula (I), via formation of an oxazolidine ring, subsequent formation of an acid chloride and reduction to the aldehyde.

16. The process as claimed in claim 3, wherein the catalytic hydrogenation is carried out at 50° C. to 150° C. at a hydrogen pressure of 1 to 20 bar in the presence of a divalent salt of ruthenium or a trivalent salt of iridium.

17. The process as claimed in claim 1, wherein the ratio by weight of substrate to catalyst is 10,000:1 to 20:1.

18. The process as claimed in claim 1, wherein the ratio by weight of substrate to catalyst is from 500:1 to 50:1.

19. The process as claimed in claim 14, wherein the ratio by weight of substrate to catalyst is from 500:1 to 50:1.

20. The process as claimed in claim 16, wherein the hydrogenation is carried out in the presence of an organic solvent.

21. The process as claimed in claim 1, wherein the hydrogenation is carried out at a temperature from 30° to 200° C.

* * * * *